(12) United States Patent
Harrison

(10) Patent No.: US 7,984,718 B2
(45) Date of Patent: Jul. 26, 2011

(54) METHOD FOR CLEANING OR LIMITING ADHESIVE

(75) Inventor: Albert Thomas Harrison, Alexandria, VA (US)

(73) Assignee: Joshua C. Harrison, Huntington Beach, CA (US)

(*) Notice: Subject to any disclaimer, the term of this patent is extended or adjusted under 35 U.S.C. 154(b) by 109 days.

(21) Appl. No.: 12/569,868

(22) Filed: Sep. 29, 2009

(65) Prior Publication Data

US 2011/0077746 A1    Mar. 31, 2011

(51) Int. Cl.
*A61B 19/00* (2006.01)
(52) U.S. Cl. ............................................. 128/899
(58) Field of Classification Search ............... 600/9–15; 128/897–899
See application file for complete search history.

(56) References Cited

U.S. PATENT DOCUMENTS

| 3,657,038 | A | | 4/1972 | Lightfoot |
| 4,035,547 | A | * | 7/1977 | Heller, Jr. et al. ............. 428/329 |
| 4,364,377 | A | * | 12/1982 | Smith ............................ 600/12 |
| 6,127,002 | A | * | 10/2000 | Callahan, Jr. et al. ........ 427/472 |
| 6,171,107 | B1 | * | 1/2001 | Milne ........................... 433/189 |
| 2003/0181984 | A1 | | 9/2003 | Abendschein |
| 2006/0035087 | A1 | * | 2/2006 | Yadav et al. ............... 428/411.1 |

FOREIGN PATENT DOCUMENTS

| WO | 9404623 | 3/1994 |
| WO | 2008091561 A1 | 7/2008 |

* cited by examiner

*Primary Examiner* — Samuel Gilbert
(74) *Attorney, Agent, or Firm* — Barcelo, Harrison & Walker LLP

(57) ABSTRACT

Methods for cleaning and limiting the extent of adhesives are disclosed. For example, a method for cleaning adhesive near a surgical site in a patient's body comprises the acts of dispensing a magnetic adhesive at a desired location at the surgical site, and applying an external magnetic field that removes a portion of the magnetic adhesive from the body of the patient outside of the desired location.

5 Claims, 5 Drawing Sheets

*300*

Open or obtain access to a surgical site in a patient's body. — *312*

Dispense a magnetic adhesive in a non-solid form at a desired location in the surgical site. — *314*

Remove a portion of the magnetic adhesive from the body of the patient, outside of the desired location, by use of an applied magnetic field. — *316*

Allow or cause the magnetic adhesive to solidify. — *318*

500

- 512 Position at least two components adjacent each other for assembly in a manufacturing apparatus.
- 514 Dispense a magnetic adhesive in a non-solid form at a desired location on a surface of at least one of the two components.
- 516 Remove a portion of the magnetic adhesive from the components and/or from the apparatus, outside of the desired location, by use of an applied magnetic field.
- 518 Allow or cause the magnetic adhesive to solidify.

*Fig . 5*

METHOD FOR CLEANING OR LIMITING ADHESIVE

FIELD OF THE INVENTION

The present invention relates generally to methods to adhere objects and specifically to methods to adhere objects where the control of the spread of the adhesive is important.

BACKGROUND

The use of magnetic adhesives has been disclosed in the art. For example, Kassab and Navia disclosed a surgical use of a magnetic endograft in a lumen, positioned inside the aorta, to attract a magnetic glue-like substance injected outside the aortic wall for endovascular aneurysm repair. See WO 2008/091561 to Kassab and Navia, incorporated herein by reference. However, no method for cleaning unwanted adhesive near a surgical site in a patient's body was taught or suggested by Kassab and Navia. Most other disclosures related to magnetic adhesives have concerned magnetic excitation of ferromagnetic particles embedded in an adhesive to heat and thereby accelerate curing of the adhesive, and/or the enhancement of the magnetic flux carrying capacity of the adhesive after it is cured. Ferrofluidic lubricants have also been disclosed, as have seals to contain such ferrofluidic lubricants.

However, there are many situations of commercial and/or medical importance where the extent of an adhesive must be carefully controlled to prevent undesired spread, and/or where undesired spread of adhesive must be carefully and thoroughly cleaned.

For example, adhesive has been used in certain orthopedic surgical procedures, such as an orthopedic surgical procedure to replace a natural but pathologic patello-femoral joint with an artificial patello-femoral joint or prosthesis. Various such methods have been used or proposed, such as that described in U.S. Patent Application Publication 2003/0181984 to Abendschein (teaching a patello-femoral joint replacement method in which an adhesive is used to bond the underside of a femoral implant to a prepared anterior surface of the femur, and incorporated herein by reference). Also for example, the use of adhesive has been employed in orthopedic surgical procedures to replace a natural but pathologic hip joint with an artificial hip joint or prosthesis (see, e.g. Japanese Patent JP 2528572 to Lawes).

In such surgical procedures, it is desirable that any adhesive that is used remain in a desired region (e.g. near the interface between the patient's bone and a surface of the prosthesis or a joining fastener), and not spread into other tissues or regions of the patient's body. However, in certain contemporary orthopedic surgical procedures, the physician must perform additional steps to contain the extent of the adhesive used, and in some cases the surgery may become more invasive to clean adhesive that has undesirably spread to other tissues. Hence, there is a need in the art for an improved method to control and limit the spread of adhesive during surgical procedures. There is also a need in the art for an improved method to clean or remove unwanted adhesive from a patient's tissues during or after a surgical procedure in which an adhesive is used.

Also for example, controlling the spread of adhesive for assembling or joining components in a reduced gravity environment (e.g. outer space) can be important, because the spread of unwanted adhesive droplets may contaminate optical lenses and/or interfere with or cause failures in related or unrelated systems. Hence, there is a need in the art for methods to clean or limit the extent of adhesives in outer space assembly and repair operations.

Also, for example, in the manufacture of hard disk drives, the magnetic recording head is adhered to the tongue of a thin laminated flexure by an adhesive (e.g. a UV-curable or electrically conductive epoxy). However it is important that the adhesive does not spread beyond a desired area on the flexure tongue, or else the adhesive might contaminate the disk drive or interfere with subsequent disk drive fabrication steps (e.g. the electrical connection of the head to conductive traces on the thin laminated flexure). Hence, geometrical features have been disclosed, which have been etched or deposited on the thin laminated flexure to control the spread of the adhesive. Such geometrical features, however, may not benefit or be compatible with other requirements for the laminated flexure structure. Accordingly, there is a need in the art for an improved method for controlling the spread of adhesive in commercial manufacturing processes. There is also a need in the art for an improved method to clean or remove unwanted adhesive from fabricated components and/or manufacturing apparatuses during or after commercial manufacturing processes.

SUMMARY

Methods for cleaning and limiting the extent of adhesives are disclosed. For example, a method for cleaning adhesive near a surgical site in a patient's body comprises the acts of dispensing a magnetic adhesive at a desired location at the surgical site, and applying an external magnetic field that removes a portion of the magnetic adhesive from the body of the patient outside of the desired location.

BRIEF DESCRIPTION OF THE DRAWINGS

FIG. 5 is a flow chart depicting an example method to clean unwanted adhesive, according to an embodiment of the present invention, as employed in a manufacturing application.

DESCRIPTION OF THE PREFERRED EMBODIMENTS

Figure 1:
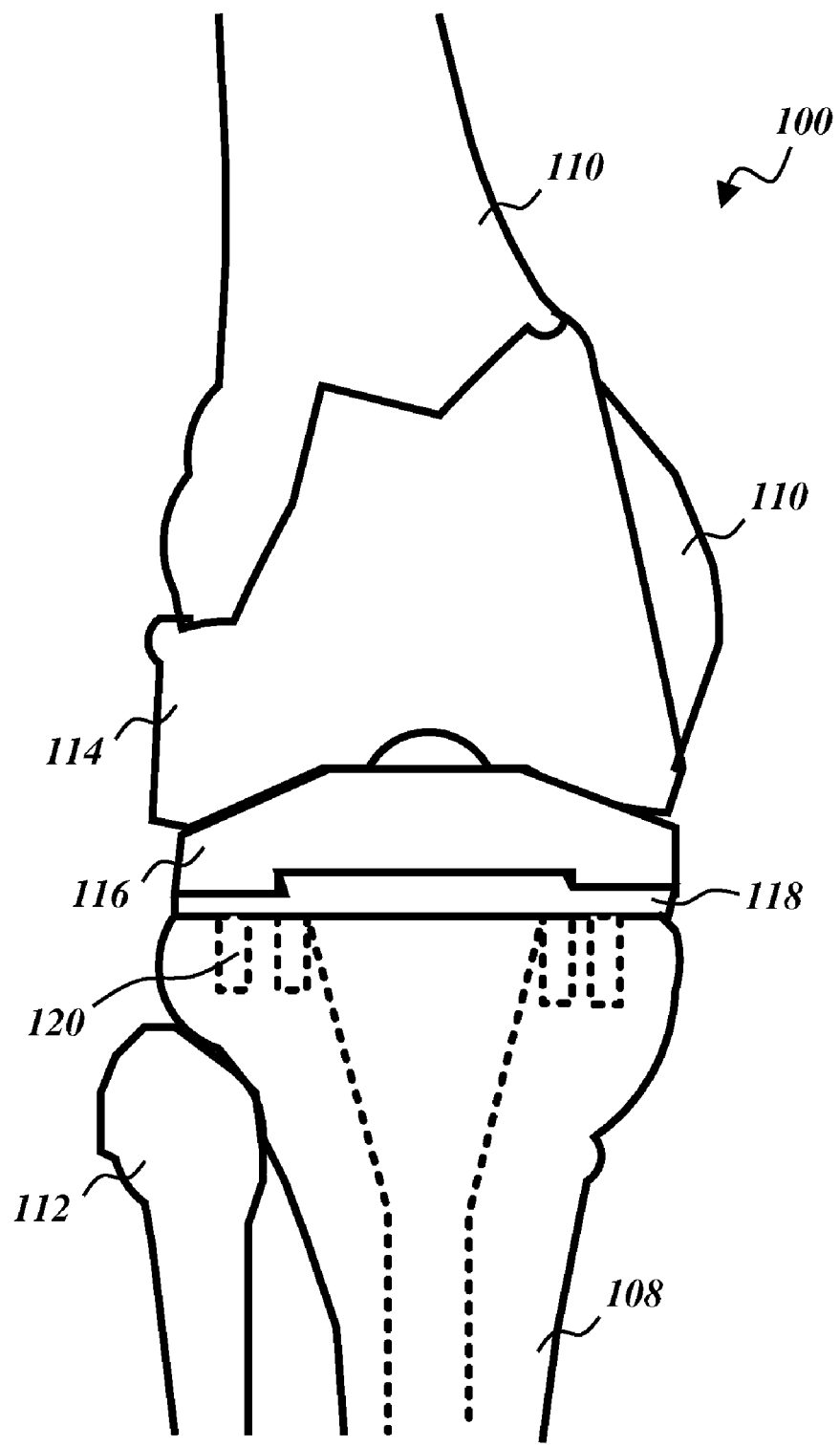
FIG. 1 depicts an artificial patello-femoral joint to which a method according to an embodiment of the present invention may be applied.

FIG. 1 depicts an artificial patello-femoral joint 100 to which a method according to an embodiment of the present invention may be applied. A femoral implant 114 may be bonded to the femur 110 by an adhesive. The femoral implant 114 forms a patello-femoral joint with bearing pad 116 and patello implant 118. The patello implant 118 is affixed to the tibia 108 (and thereby also coupled to the fibula 112), for example by fasteners 120 that extend into the tibia 108.

Figure 2:
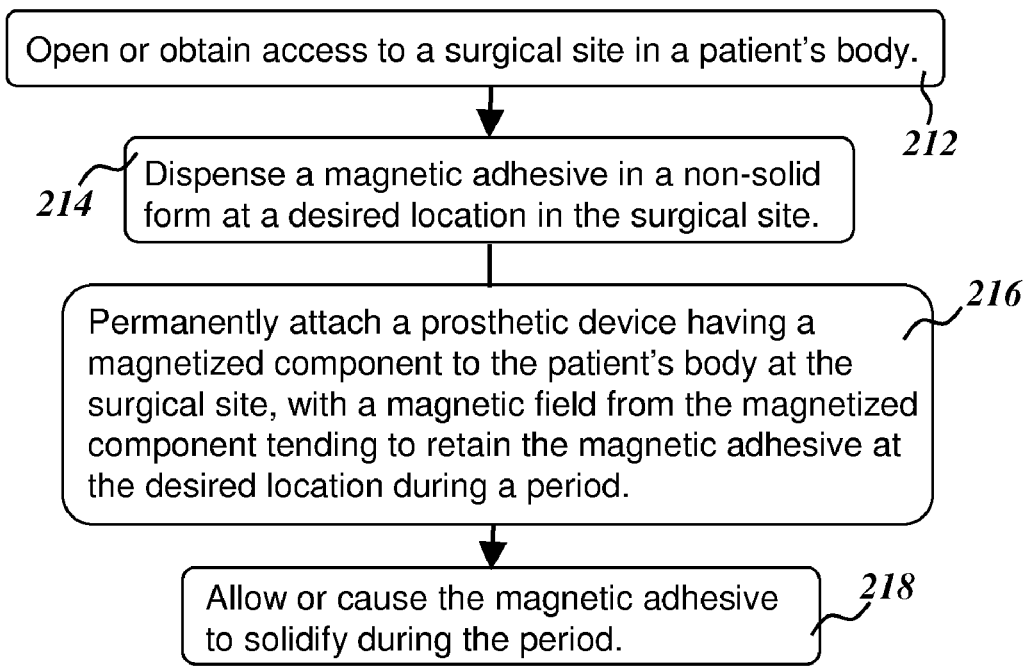
FIG. 2 is a flow chart depicting an example method to limit an extent of adhesive, according to an embodiment of the present invention, as employed in a surgical application.

FIG. 2 is a flow chart depicting an example method 200 to limit an extent of adhesive, according to an embodiment of the present invention, as employed in a surgical application.

In step 212, a surgical site in a patient's body is opened or otherwise accessed. For example, in knee or hip joint replacement surgery, one or more incisions may be opened at the affected joint and the surgical site may be accessed directly, while in arthroscopic surgery or intra-vascular surgery, access to the surgical site may be remote. Then in step 214, a magnetic adhesive is dispensed in a non-solid form at a desired location at a surgical site in a patient's body. For example, the magnetic adhesive may be dispensed in liquid form on a surface of a conventional femoral implant or on a surface of the femur. The magnetic adhesive is preferably a non-magnetic adhesive (e.g. a conventional epoxy) doped with a magnetic powder (e.g. a ferrite powder or other powder comprising Fe, Ni, Sr, Ba, Mn, Co, Zn, and/or a rare earth magnetic material).

In step 216, a prosthetic device (e.g. a component of an artificial patello-femoral joint) having a magnetized component (e.g. a femoral implant) is permanently attached to the patient's body at the surgical site, with a magnetic field from the magnetized component tending to retain the magnetic adhesive at the desired location during a period. For example, a portion of a femoral implant component of an artificial patello-femoral joint may include permanently magnetized ferromagnetic material, where the ferromagnetic component has a remnant field that tends to retain the magnetic adhesive adjacent the interface between the femoral implant and the femur for a period.

In step 218, the magnetic adhesive is solidified during the period, which means that the magnetic adhesive is either passively allowed or actively caused to solidify during the period. Note that, in the embodiment of FIG. 2, step 218 may begin during or after step 216, and step 216 may commence after or before step 214.

Figure 3:
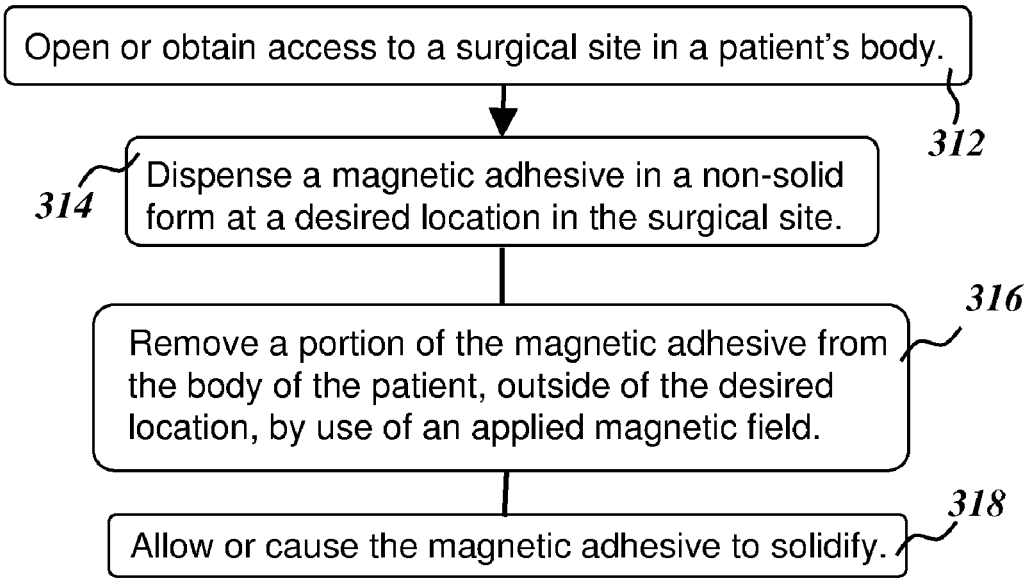
FIG. 3 is a flow chart depicting an example method to clean unwanted adhesive, according to an embodiment of the present invention, as employed in a surgical application.

FIG. 3 is a flow chart depicting an example method 300 to clean unwanted adhesive, according to an embodiment of the present invention, as employed in a surgical application.

In step 312, a surgical site in a patient's body is opened or otherwise accessed. For example, in knee or hip joint replacement surgery, one or more incisions may be opened at the affected joint and the surgical site may be accessed directly, while in arthroscopic surgery or intra-vascular surgery, access to the surgical site may be remote. Then in step 314, a magnetic adhesive is dispensed (preferably in a non-solid form) at a desired location at a surgical site in a patient's body. For example, the magnetic adhesive may be dispensed in a paste or gel form on a surface of a conventional femoral implant or on a surface of the femur. The magnetic adhesive is preferably a non-magnetic adhesive (e.g. a conventional epoxy) doped with a magnetic powder (e.g. a ferrite powder or other powder comprising Fe, Ni, Sr, Ba, Mn, Co, Zn, and/or a rare earth magnetic material).

In step 316, a portion of the magnetic adhesive is removed from the body of the patient, outside of the desired location, by use of an applied magnetic field. In certain embodiments, the external magnetic field may be applied before curing of the magnetic adhesive, so that the magnetic adhesive is removed in non-solid form. In certain other embodiments, the external magnetic field may be applied after curing of the magnetic adhesive, so that the magnetic adhesive is removed in solid form.

In certain embodiments of the example method shown in FIG. 3, the external magnetic field may be created by an electromagnet that is mounted outside the body of the patient. For example, an electromagnet may be mounted on an adjustable support outside the patient's body near the surgical site, so that its magnetic field is continuously applied to a region outside the desired bonding location to immediately and continuously remove any magnetic adhesive droplets that spread to that region. In certain alternative embodiments, the external magnetic field may be created by a permanent magnet that is a component of a hand-held surgical instrument, and the surgeon may sweep the permanent magnet through or over a region outside the desired bonding location to attract and thereby remove any unwanted magnetic adhesive droplets. Note that a switched electromagnet may be utilized in the aforementioned embodiments to facilitate removal of the adhesive from the hand-held surgical instrument and/or externally mounted magnet.

In step 318, the magnetic adhesive is solidified, which means that the magnetic adhesive is either passively allowed or actively caused to solidify. Note that, in the example method of FIG. 3, step 318 may begin during or after step 316, and step 316 may commence during or after step 314.

Figure 4:
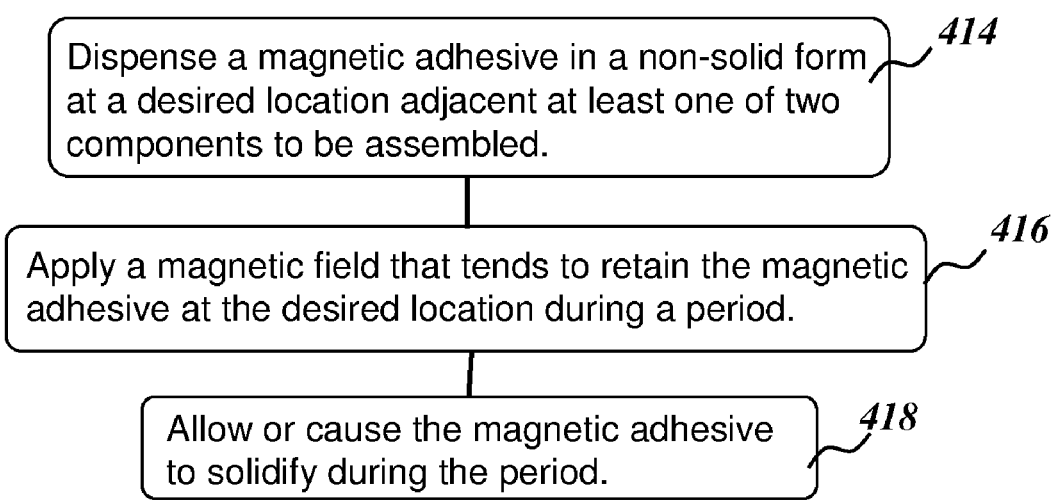
FIG. 4 is a flow chart depicting an example method to limit an extent of adhesive, according to an embodiment of the present invention, as employed in an outer space assembly application.

FIG. 4 is a flow chart depicting an example method 400 to limit the extent of adhesive, according to an embodiment of the present invention, as employed in a manufacturing or outer space assembly application.

In step 414, a magnetic adhesive is dispensed in a non-solid form at a desired location adjacent at least one of two components to be assembled. For example, in a space assembly application, a magnetic adhesive may be dispensed in non-solid form on the periphery of a lens, or conventional photo-voltaic cell or array (where it is important that the spread of the adhesive be limited so that stray adhesive does not contaminate a conventional satellite's lens).

In step 416, a magnetic field is applied which tends to retain the magnetic adhesive at the desired location during a period. Note that a magnet that is external to the two components being assembled may apply the magnetic field, or the magnetic field may be applied by a magnetic component that is a part of one of the components being assembled. The magnet may be a conventional permanent magnet or a conventional electromagnet (e.g. a switched electromagnet).

In step 418, the magnetic adhesive is solidified during the period, which means that the magnetic adhesive is either passively allowed or actively caused to solidify during the period. Note that, in the embodiment of FIG. 4, step 418 may begin during or after step 416, and step 416 may commence after or before step 414.

FIG. 5 is a flow chart depicting an example method 500 to clean unwanted adhesive, according to an embodiment of the present invention, as employed in a manufacturing application. In step 512, at least two components are positioned adjacent each other for assembly in a manufacturing apparatus. For example, in a hard disk drive manufacturing application, the manufacturing apparatus may be a conventional head-gimbal assembly tool that positions a conventional AlTiC slider on a flexure tongue of a conventional suspension assembly.

In step 514, a magnetic adhesive is dispensed in a non-solid form at a desired location adjacent at least one of two components to be assembled. For example, in a hard disk drive manufacturing application, a magnetic adhesive may be dispensed in liquid form on the flexure tongue of a conventional suspension assembly, or alternatively on the top surface of a conventional AlTiC slider to be bonded on such a suspension assembly (where it is important that the spread of the adhesive be limited so that stray adhesive particles from the instant or previous assemblies do not contaminate any head-disk interface).

In step 516, a portion of the magnetic adhesive is removed from the components and/or from the apparatus, outside of the desired location, by use of an applied magnetic field. In certain embodiments, the external magnetic field may be applied before curing of the magnetic adhesive, so that the magnetic adhesive is removed in non-solid form. In certain other embodiments, the external magnetic field may be applied after curing of the magnetic adhesive, so that the magnetic adhesive is removed in solid form.

In certain embodiments of the example method shown in FIG. 5, the external magnetic field may be created by an electromagnet that is mounted on the manufacturing apparatus but separate from the components to be assembled, so that its magnetic field is continuously applied to a region outside the desired bonding location to remove any magnetic adhesive droplets as they spread to that region. In certain alternative embodiments, the external magnetic field may be created by a permanent magnet that is a component of a hand-held cleaning tool, and a human operator may sweep the permanent magnet through or over a region outside the desired bonding location to attract and thereby remove any unwanted magnetic adhesive droplets. Note that a switched electromagnet may be utilized in the aforementioned embodiments to facilitate removal of the adhesive from the hand-held cleaning tool and/or externally mounted magnet.

In step 518, the magnetic adhesive is solidified, which means that the magnetic adhesive is either passively allowed or actively caused to solidify. Note that, in the example method of FIG. 5, step 518 may begin before or after step 516, and step 516 may commence during or after step 514. Also, step 512 may precede or follow step 514.

In the foregoing specification, the invention is described with reference to specific exemplary embodiments, but those skilled in the art will recognize that the invention is not limited to those. It is contemplated that various features and aspects of the invention may be used individually or jointly and possibly in a different environment or application. The specification and drawings are, accordingly, to be regarded as illustrative and exemplary rather than restrictive. "Comprising," "including," and "having," are intended to be open-ended terms.

We claim:

1. A surgical method comprising the acts of:
dispensing a magnetic adhesive at a desired location at a surgical site in the body of a patient; and
applying an external magnetic field that removes a portion of the magnetic adhesive from the body of the patient outside of the desired location;
wherein the external magnetic field is applied before curing of the magnetic adhesive, so that the magnetic adhesive is removed in non-solid form.

2. A surgical method comprising the acts of:
dispensing a magnetic adhesive at a desired location at a surgical site in the body of a patient; and
applying an external magnetic field that removes a portion of the magnetic adhesive from the body of the patient outside of the desired location;
wherein the external magnetic field is created by a permanent magnet that is a component of a hand-held surgical instrument.

3. The method of claim 2 wherein the magnetic adhesive is a non-magnetic adhesive doped with a magnetic powder.

4. The method of claim 3 wherein the magnetic powder is a ferrite powder.

5. The method of claim 3 wherein the non-magnetic adhesive is an epoxy adhesive.

* * * * *